United States Patent [19]

Skotnicki et al.

[11] Patent Number: 4,728,734

[45] Date of Patent: Mar. 1, 1988

[54] C-3'THIOIMINOSULFONYL CEPHALOSPORIN ANALOGS

[75] Inventors: Jerauld S. Skotnicki, Chadds Ford; Donald P. Strike, St. Davids, both of Pa.

[73] Assignee: American Home Products Corporation, New York, N.Y.

[21] Appl. No.: 801,645

[22] Filed: Nov. 25, 1985

[51] Int. Cl.$^4$ ................ C07D 501/36; A61K 31/545
[52] U.S. Cl. ................................................. 540/227
[58] Field of Search ........................................ 540/227

[56] References Cited

U.S. PATENT DOCUMENTS 4,614,819 9/1986 Nagai et al. ................ 540/227 X

OTHER PUBLICATIONS

Skotnicki, et al., Chem. Abstracts 105 (1986) entry 226119u.
Horrii, et al., Chem. Abstracts 90 (19) entry 168628t.

*Primary Examiner*—Donald G. Daus
*Assistant Examiner*—William A. Teoli, Jr.
*Attorney, Agent, or Firm*—George Tarnowski

[57] ABSTRACT

There are disclosed novel antibacterial compounds having the formula

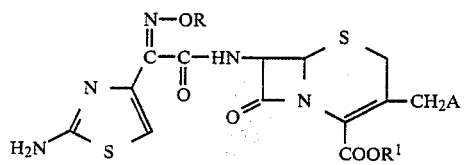

wherein
R is hydrogen, lower alkyl, lower alkenyl, lower alkynyl, cyclo lower alkyl, aryl of 6-12 carbon atoms, all the said foregoing groups being optionally substituted with carboxy, lower alkoxycarbonyl, phenoxycarbonyl, amino, mono- or di-lower alkyl substituted amino, hydroxy, lower alkoxy, phenoxy, carbamoyl, lower alkyl carbonyl, benzoyl, cyano, nitro, formamido, lower alkanoylamino or benzamido;

$R^1$ is hydrogen, lower alkyl or an alkali metal cation;

A is

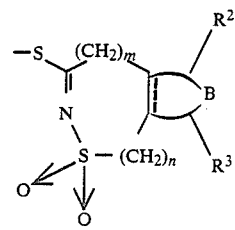

$R^2$ and $R^3$ are each individually lower alkyl, carboxy, lower alkoxycarbonyl, phenoxycarbonyl, amino, mono- or di-lower alkyl substituted amino, hy, lower alkoxy, phenoxy, carbamoyl, mono- or di-lower alkyl substituted cabamoyl, lower alkylcarbonyl, benzoyl, cyano, nitro, lower alkanoylamino or benzamido;

m=0-1;
n=0-1;
B represents

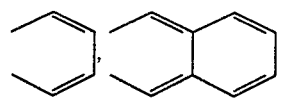

or a 5- or 6- membered unsaturated aza-, diaza-, triaza-, tetraza-, thia-, thiaza-, oxathia-, oxathiaza-, oxa-, dioxa-, oxaza- or, oxadiazacyclic moiety; and the dotted line denotes an optional double bond.

3 Claims, No Drawings

C-3'THIOIMINOSULFONYL CEPHALOSPORIN ANALOGS

The present invention is directed to C-3'-substituted cephalosporin derivatives having antibacterial activity. The compounds of the invention have the formula

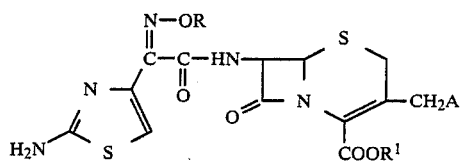

wherein

R is hydrogen, lower alkyl, lower alkenyl, lower alkynyl, cyclo lower alkyl, aryl of 6–12 carbon atoms, all the said foregoing groups being optionally substituted with carboxy, lower alkoxycarbonyl, phenoxycarbonyl, amino, mono- or di-lower alkyl substituted amino, hydroxy, lower alkoxy, phenoxy, carbamoyl, lower alkyl carbonyl, benzoyl, cyano, nitro, formamido, lower alkanoylamino or benzamido;

$R^1$ is hydrogen, lower alkyl or an alkali metal cation;

A is

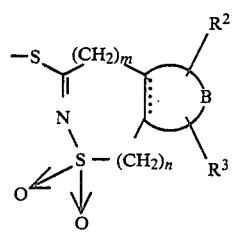

$R^2$ and $R^3$ are each individually lower alkyl, carboxy, lower alkoxycarbonyl, phenoxycarbonyl, amino, mono- or di-lower alkyl substituted amino, hydroxy, lower alkoxy, phenoxy, carbamoyl, mono- or di-lower alkyl substituted cabamoyl, lower alkylcarbonyl, benzoyl, cyano, nitro, lower alkanolyamino or benzamido;

m=0–1;

n=0–1;

B represents

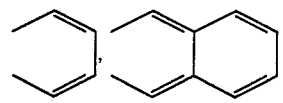

or a 5- or 6-membered unsaturated aza-, diaza-, triaza-, tetraza-, thia-, thiaza-, oxathia-, oxathiaza-, oxa-, dioxa-, oxaza- or oxadiazacyclic moiety; and the dotted line denotes an optional double bond.

The terms "lower alkyl" and "lower alkoxy" refer to unbranched or branched moieties having 1–6 carbon atoms in the carbon chain. "Lower alkanoyl" refers to moieties having 1–6 carbon atoms in a carbon chain attached to a carbonyl group. The terms, "lower alkenyl" and "lower alkynyl" refer to unbranched or branched moieties of the requisite degree of unsaturation having 2–6 carbon atoms in the carbon chain. The term "halo" refers to fluoro, chloro and bromo. The term "alkali metal cation" refers to Na+ and K+.

When B denotes a 5- or 6-membered unsaturated aza-, diaza-, triaza-, tetraza-, thia-, thiaza-, oxathia-, oxathiaza-, oxa-, dioxa-, oxaza- or oxadiazacyclic moiety, this refers to but is not limited to the moieties which when fused as shown in substituent A, can be a pyrrole, imidazole, triazole, tetrazole, pyridine, pyrimidine, pyrazine, pyridazine, triazine, tetrazine, thiazole, isothiazole, thiazine, oxathiole, oxathiazine, furan, pyran, dioxin, oxazole, oxazine, isoxazine, oxadiazole, oxadiazine and the like.

The compounds of the invention can be prepared by reacting a suitably protected cephalosporin derivative with a reactive species of the desired substituent A. The following reaction scheme, in which A is a thienoisothiazole, is representative of the preparative scheme in question:

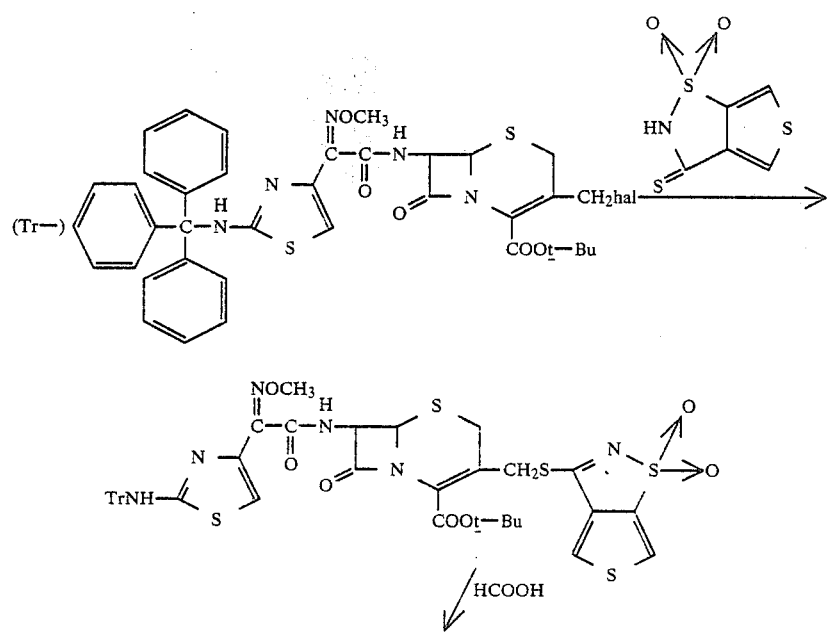

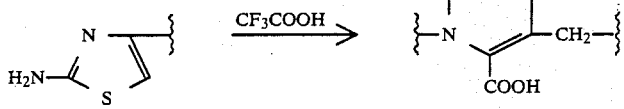 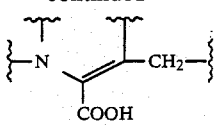

wherein hal refers to iodo, bromo or chloro. The initial reactive cephalosporin derivative has a suitably protected carboxyl group at the C-2' position and the amino group on the thiazole ring is also suitably protected. The protecting groups used include any readily displacable groups known in the art for protecting primary amines and carboxylic acid groups. The exemplified protecting groups are triphenylmethyl (Tr) and t-butyl, respectively, and these groups are preferred. In the above scheme, the triphenylmethyl group is displaced with formic acid leaving a primary amine group on the thiazole ring, while in the last step the t-butyl group is displaced with trifluoroacetic acid, giving a carboxylic acid group in the cephalosporin C-2' position.

The starting cephalosporin derivative having the formula

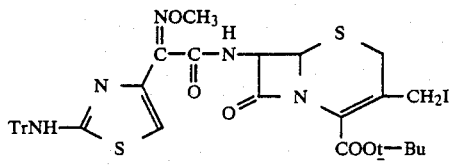

can be prepared according to the method described in Bonjouklian and Phillips, *Tetrahedron Letters*, 22, 3915 (1981). The A moieties are well-known in the art and are either commercially available or can be prepared by conventional methods. The R moieties are known in the art (see e.g. U.S. Pat. No. 4,420,477).

The compounds of the invention are antibacterial agents effective against a variety of pathogenic Gram-positive and Gram-negative bacterial organisms, including penicillin-resistant Staphylococcus. Thus, the antibacterial compounds of the invention are useful in the therapeutic treatment of bacterial infections in poultry and animals, including man, as well as being useful as nutritional supplements in animal feeds. The compounds of the invention are particularly active against the Gram negative bacteria and exhibit β-lactamase stability.

Because of their antibacterial properties, the compounds of the invention can be formulated into therapeutically valuable compositions comprising compounds of the invention and pharmacologically acceptable carriers. The latter term contemplates usual and customary substances employed to formulate solid, oral unit dosages for pharmacological purposes. The term also includes those substances employed to formulate either in unit dose or multidose form, oral and injectable suspensions and solutions, either directly or for reconstitution before administration.

To formulate dosages for administration according to this invention the compounds of the invention can be compounded into oral dosage forms such as tablets, capsules and the like. This is done by combining the compounds with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter, and the like. Diluents, flavoring agents, solubilizers, lubricants, suspending agents, binder, tablet-disintegrating agents and the like may be employed. The active ingredient may be encapsulated with or without other carriers. In all cases, the proportion of active ingredients in said compositions both solid and liquid will be at least sufficient to impart antibacterial activity thereto on oral administration.

The compounds may also be injected parenterally, in which case they are used in the form of a sterile solution containing other solutes, for example, enough saline or glucose to make the solution isotonic. The compounds may also be used topically and for this purpose they may be formulated in the form of dusting powders, solutions, creams or lotions in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with samll dosages less than the optimum dose of the compound. Thereafter, the dosage is increased until the optimum effect under the circumstances is reached. In general, the compounds of the invention are most desirably administered at a concentration level that will generally afford effective results without causing any harmful or deleterious side effects.

The antibacterial activity of the compounds of the invention may be demonstrated by a standard pharmaceutical procedure which is described fully following the below presented examples directed to the preparation of the compounds useful in the invention.

PREPARATION OF STARTING CEPHALOSPORIN INTERMEDIATES (6R,7R)-3-(Iodomethyl)-7-[[(Z)-(methoxyimino)[4-[(triphenylmethyl)amino]-2-thiazolyl]acetyl]amino]-8-oxo-5-thia-1-azabicyclo[4.2.0]oct-2-ene-2-carboxylic acid 1,1-dimethylethyl ester To a solution of 8.4 g (0.0111 mol) of (6R,7R)-3-acetoxymethyl-7-[[(Z)-methoxyimino)[4-[(triphenylmethyl)amino]-2-thiazolyl]acetyl]amino]-8-oxo-5-thia-1-azabicyclo[4.2.0]oct-2-ene-2-carboxylic acid 1,1-dimethylethyl ester and 100 ml of $CH_2Cl_2$ at ambient temperature uinder a nitrogen atmosphere is added dropwise 3.35 ml (4.71 g/0.0235 mmol) of trimethylsilyl iodide. The reaction mixture is stirred for 2 hours, then washed successively with cold 10% $Na_2S_2O_3$ solution, saturated $NaHCO_3$ solution, and brine, dried over $Na_2SO_4$, and concentrated in vacuo. The multicomponent residue is purified by high performance liquid chromatography (2:98/EtOAc:$CH_2Cl_2$) to afford 3.62 g (40%) of title compound: IR (KBr) 3280, 1785, 1715, 1675, 1520, 1365, 1300, 1150, and 1035 cm$^{-1}$; NMR (CDCl$_3$) 7.34 (s, 15H), 6.94–6.86 (m, 1H), 6.67 (s, 1H), 5.96–5.88 (m, 1H), 5.06 (d, 1H), 4.45 (d, 1H), 4.32 (d, 1H), 4.12 (s, 3H), 3.76 (d, 1H), 3.52 (c, 1H), 2.06 (s, 3H), and 1.56 (s, 9H).

EXAMPLE 1

(6R,7R)-7-[[(2-Amino-4-thiazolyl)(methoxyimino)acetyl]amino]-8-oxo-3-[(thieno[3,4-d]isothiazol-3-ylthio)methyl]-5-thia-1-azabicyclo[4.2.0]oct-2-ene-2-carboxylic acid $S^3,S^3$-dioxide

A.

(6R,7R)-7-[[(Methoxyimino)[2-[(triphenylmethyl)amino]-4-thiazolyl]acetyl]amino]-8-oxo-3-[(thieno[3,4-d]isothiazol-3-ylthio)methyl]-5-thia-1-azabicyclo-[4.2.0]oct-2-ene-2-carboxylic acid 1,1-dimethylethyl ester $S^3,S^3$dioxide A solution of 500 mg (0.61 mmol) of (6R,7R)-3-(iodomethyl)-7-[[(methoxyimino)[2-[(triphenylmethyl)amino]-4-thiazolyl]acetyl]amino]-8-oxo-5-thia-1-1-azabicyclo[4.2.0]oct-2-ene-2-carboxylic acid 1,1-dimethylethyl ester, 125 mg (0.61 mmol) of thiophene saccharin thione, and 2 ml of dimethylformamide is stirred at ambient temperature for three hours. The reaction mixture is poured into water. The resulting precipitate is collected and triturated with ether to afford 477 mg (87%) of the title compound as a tan solid: IR (KBr) 3400 (br), 1790, 1715, 1670, 1530, 1375, 1340, 1175, and 1040 (br) cm$^{-1}$; NMR (CDCl$_3$) δ 7.80 (d, 1H), 7.59 (d, 1H), 7.36 (s, 15H), 6.96 (s, 1H), 6.5 (s, 1H), 6.02–5.92 (m, 1H), 5.07, (d, 1H), 4.43–4.10 (m, 2H), 4.2 (s, 3H), 3.74–3.46 (m, 2H), and 1.54 (s, 9H).

B.

(6R,7R)-7[[(2-Amino-4-thiazolyl)(methoxyimino)acetyl]amino]-8-oxo-3-[(thieno[3,4-d]isothiazol-3-ylthio)methyl]-5-thia-1-azabicyclo[4.2.0]oct-2-ene-2-carboxylic acid 1,1-dimethylethyl ester $S^3,S^3$-dioxide A mixture of 460 mg (0.51 mmol) of A. above and 4 ml of HCOOH (88%) is stirred at ambient temperature for two hours. The resulting precipitate is collected and discarded. The filtrate is concentrated in vacuo to give a waxy solid. Trituration with ether affords 227 mg (68%) of the title compound as a tan solid: IR (KBr) 3350, 1780, 1710, 1660 (br), 1525, 1450, 1370, 1330, 1170, 1150, and 1030 cm$^{-1}$; NMR (DMSO-d$_6$) δ 9.65 (d, 1H), 8.55 (d, 1H), 8.41 (d, 1H), 6.78 (s, 1H), 5.92–5.82 (m, 1H), 5.12 (d, 1H), 4.53 (d, 1H), 4.13 (d, 1H), 3.87 (s, 3H), 3.57 (d, 1H), 3.41 (d, 1H), and 1.52 (s, 9H).

C.

(6R,7R)-7-[[(2-Amino-4-thiazolyl)(methoxyimino)acetyl]amino]-8-oxo-3-[(thieno-[3,4-d]isothiazol-3-ylthio)methyl]-5-thia-1-azabicyclo[4.2.0]oct-2-ene-2-carboxylic acid $S^3,S^3$-dioxide, trifluoroacetate salt A solution of 171 mg (0.26 mmol) of B. above, 0.5 mol of anisole, and 5 ml of CF$_3$COOH is stirred at 0° C. for three hours. The reaction mixture is concentrated under high vacuum, to give a brown oil. Trituration with ether furnishes 137 mg (88%) of the title compound as a yellow powder: IR (KBr) 3350 (br), 1780, 1710, 1670 (br), 1460, 1330, 1200, 1170, 1040, and 935 cm$^{-1}$; NMR DMSO-d$_6$) δ 9.71 (d, 1H), 8.57 (d, 1H), 8.43 (d, 1H), 6.86 (s, 1H), 5.92–5.8 (m, 1H), 5.21 (d, 1H), 4.47 (d, 1H), 4.23 (d, 1H), 3.88 (s, 3H), and 3.66–3.338 (m, 2H).

EXAMPLE 2

The compounds of the invention are tested for their antibacterial activity. The test is carried out as follows:

The organisms used in the test comprise the following:

Staphylococcus aureus (penicillin-sensitive and resistant), Pseudomonas aeruginosa, Escherichia coli, Salmonella pneumoniae, Bordetella bronchiseptica, Proteus vulgaris, P. mirabilis, Acinetobacter calcoaceticus.

Test organisms may be added or deleted in order to reflect current clinical patterns of antibiotic susceptibility or shifts in pathogenic potential.

Organisms are normally grown for 18 hours in Brain Heart Infusion at 35° C. Cultures are adjusted with saline to MacFarland No. 1.5 standard prior to use.

Stock concentrations (e.g. 2,5000 μg or units per ml) are prepared in a suitable vehicle. Two-fold dilutions are made. One ml quantities of each dilution are incorporated in 9 ml of the appropriate agar (e.g. Seed) in sterile Petri plates. The hardened surface is inoculated with test organisms by use of a Steers replicating device. The plates are incubated (e.g. 18 hours at 35° C.) and activity is determined.

The least amount of material that completely inhibits the test organisms is the Minimal Inhibitory Concentration (MIC), which is expressed in μg or units per ml.

The compounds of the invention, when tested according to the above outlined procedures, give the results summarized in Table 1.

TABLE 1

| Organism | Compound of Example No. MIC (μg/ml) | |
|---|---|---|
| | 1 B. | 1 C. |
| Staphylococcus aureus ATCC 29213 | 128 | 32 |
| Streptococcus faecalis ATCC 29212 | >256 | 256 |
| Enterobacter cloacae ATCC 13047 | >256 | 32 |
| Escherichia coli ATCC 25922 | 8 | 2 |
| Klebsiella pneunomiae KL-1 | 2 | <1 |
| Proteus vulgaris A 84354 1 | 2 | <1 |
| Pseudomonas aeruginosa ATCC 27853 | >256 | >256 |
| Serratia marcescens ATCC 13880 | 32 | 2 |

The results show the compounds of the invention to have anti-bacterial activity against the organisms used in the test procedures, in particular against Gram-negative organisms.

What is claimed is:

1. A compound having the formula

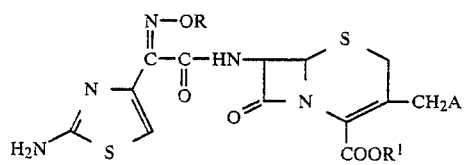

wherein

R is hydrogen, lower alkyl, lower alkenyl, lower alkynyl, cyclo lower alkyl or phenyl;

R$^1$ is hydrogen, lower alkyl or an alkali metal cation;

A is

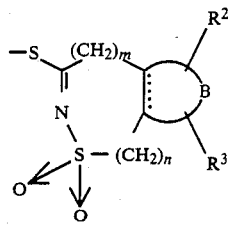

R² and R³ are each individually lower alkyl, carboxy, lower alkoxycarbonyl, phenoxycarbonyl, amino, mono- or di-lower alkyl substituted amino, hydroxy, lower alkoxy, phenoxy, carbamoyl, mono- or di-lower alkyl substituted cabamoyl, lower alkylcarbonyl, benzoyl, cyano, nitro, lower alkanolyamino or benzamido;
m=0-1;
n=0-1;

B represents

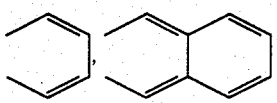

or a thieno or pyrido moiety; and the dotted line denotes an optical double bond.

2. The compound of claim 1, having the name (6R,7R)-7-[[(2-amino-4-thiazolyl)(methoxyimino)acetyl]amino]-8-oxo-3-[(thieno[3,4-d]isothiazol-3-ylthio)methyl]-5-thia-1-azabicyclo[4.2.0]oct-2-ene-2-carboxylic acid 1,1-dimethylethyl ester $S^3,S^3$-dioxide.

3. The compound of claim 1, having the name (6R,7R)-7-[[(2-amino-4-thiazolyl)(methoxyimino)acetyl]amino]-8-oxo-3-[(thieno[3,4-d]isothiazol-3-ylthio)methyl]-5-thia-1-azabicyclo[4.2.0]oct-2-ene-2-carboxylic acid $S^3,S^3$-dioxide.

* * * * *